United States Patent [19]

Tanihara et al.

[11] Patent Number: 5,679,371

[45] Date of Patent: Oct. 21, 1997

[54] WOUND DRESSING

[75] Inventors: Masao Tanihara; Yoshiharu Fukunishi, both of Kurashiki; Hisao Kinoshita, Ikoma, all of Japan

[73] Assignee: Kuraray Co., Ltd., Kurashiki, Japan

[21] Appl. No.: 569,351

[22] Filed: Dec. 8, 1995

[30] Foreign Application Priority Data

Dec. 8, 1994 [JP] Japan .................. 6-304449

[51] Int. Cl.$^6$ .................. A61L 15/24; C08F 8/12
[52] U.S. Cl. .................. 424/443; 525/61
[58] Field of Search .................. 424/443, 444, 424/445, 446

[56] References Cited

U.S. PATENT DOCUMENTS 5,480,717  1/1996  Kundel .................. 424/445

*Primary Examiner*—Peter F. Kulkosky
*Attorney, Agent, or Firm*—Oblon, Spivak, McClelland, Maier & Neustadt, P.C.

[57] ABSTRACT

The present invention provides a wound dressing composed of a hydrogel with the principal component being a vinyl alcohol polymer of a viscosity average polymerization degree of 300 or more, wherein the vinyl alcohol polymer contains 5 to 50 mol % of one or more vinyl ester units represented by the following formula (I):

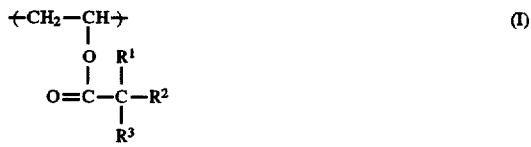

and the vinyl alcohol polymer has a block character ($\eta$) of 0.6 or less, the block character being represented by the following mathematical formula (II);

$$\eta = [OH, VES]/2[OH][VES] \qquad (II)$$

Because the wound dressing of the present invention is excellent in terms of transparency, flexibility, hot water resistance, water absorption, and safety, the dressing is useful for the treatment and promotion of the healing of wounds including general wounds such as abrasions, cuts and acne; surgery wounds such as excision wounds and dermabrasions; burns; ulcers; and pressure sores.

17 Claims, No Drawings

WOUND DRESSING

BACKGROUND OF THE INVENTION

1. Field of the Invention

The present invention relates to a wound dressing. Because the wound dressing of the present invention is excellent in terms of transparency, flexibility, hot water resistance, water absorption, and safety, the dressing is useful for the treatment and promotion of the healing of wounds including general wounds such as abrasions, cuts and acne; surgery wounds such as excision wounds and dermabrasions; burns; ulcers; and pressure sores.

2. Description of the Prior Art

Gauze and ointments have been used conventionally for the treatment of wounds such as trauma, burns, ulcers and pressure sores, and they have effects of absorbing exudate and preventing the infiltration of extraneous bacteria and the like.

In recent years, it has been indicated that a variety of growth factors (bFGF, TGFβ and the like) promoting healing are present in the exudate from wounds (see Howell, J. M., Current and Future Trends in Wound Healing, Emerg. Med. Clin. North Amer., 10, 655–663 (1992)). Therefore, attention has been focused on an occlusive dressing capable of exerting a wound healing effect by retaining such growth factors on wounds (see Eaglstein, W. E., Experience with biosynthetic dressings, J. Am. Acad. Dermatol., 12, 434–440 (1985)). Polyurethane films, hydrocolloids, non-woven fabrics composed of alginate fiber, polyvinyl alcohol sponges, polyvinyl alcohol hydrogels, polyethylene glycol hydrogels, polyacrylamide hydrogels and the like, have been known as such occlusive dressing.

As a wound dressing composed of polyvinyl alcohol hydrogel, furthermore, a wound dressing (sometimes abbreviated as "wound dressing A" hereinafter; see Japanese Patent Laid-open No. Sho 58-92359) is known that is composed of a type of polyvinyl alcohol hydrogel (sometimes abbreviated as "hydrogel A" hereinafter) produced by freezing and dehydrating under reduced pressure an aqueous polyvinyl alcohol solution having a saponification degree of 95 mol % or more (a molar ratio of the vinyl ester unit below 5%) and a viscosity average polymerization degree of 1500 or more. Additionally, a semi-transparent hydrogel composition (sometimes abbreviated as "hydrogel B" hereinbelow; see European Patent No. 0,583,170 A1) produced by physically crosslinking polyvinyl alcohol with a complexing agent, a hydrogel (sometimes abbreviated as "hydrogel C" hereinbelow; see Japanese Patent Laid-open No. Hei 3-215417) produced by crosslinking polyvinyl alcohol with radiation, a gelling substrate (sometimes abbreviated as "hydrogel D" hereinbelow; see U.S. Pat. No. 5,187,226) composed of a vinyl alcohol polymer of a syndiotacticity of 55% or more, and the like, have been known as other polyvinyl alcohol hydrogels.

Although polyurethane film to be used as a wound dressing has higher transparency and greater occlusive potency, the film does not have any water absorptivity, so that the film is not applicable to wounds with much exudate. Because hydrocolloids, nonwoven fabrics composed of alginate fiber, polyvinyl alcohol sponges, and polyvinyl alcohol hydrogels, are all opaque even though they have the potency of retaining exudate, wounds cannot be observed through them. Additionally, hydrocolloid dressings are problematic because the principal component thereof is retained in tissues for a long term, involving the onset of chronic inflammation (Young, S. R. et al., Comparison of the effect of semi-occlusive polyurethane dressings and hydrocolloid dressings on dermal repair: 1. Cellular changes, J. Invest. Dermatol., 97, 586–592 (1991)). Some types of polyethylene glycol hydrogel and polyacrylamide hydrogel have good transparency, but they are not biodegradable because they are synthetic polymers. Therefore, they are retained in wounds, involving the risk of inducing chronic inflammatory reactions. The raw material monomers of the two gels are so highly toxic that the remaining monomers and the degradation components of the gels may trigger the onset of toxicity.

When these occlusive dressings are used, furthermore, the moist environment is a suitable medium to induce rapid bacterial growth leading to the development of severe infection. For the treatment, antibiotics may systemically or locally be administered, but the wounds infected with bacteria are generally poor in terms of blood circulation; and an effective therapeutic amount of antibiotics never reaches the wounds when administered systemically, while side effects due to cytotoxicity of anti-bacterial agents may be a concern when administered locally.

Because wound dressing A composed of hydrogel A is opaque, wounds cannot be observed through the dressing applied onto the wounds although the wound dressing A has an excellent mechanical strength. The dressing is solubilized by steam sterilization (at 121° C. for 20 minutes). Additionally, the wound dressing A has a drawback in that it is poor in safety because of the higher levels of extracted products therefrom at a temperature where the wound dressing A is not solubilized. Hydrogel B at a thickness of 1,000 μm or less is semi-transparent, but for use as a wound dressing, wounds can be observed through the gel only with much difficulty. It should be required that the hydrogel B have a thickness above 1,000 μm so that the gel might exert satisfactory water absorptivity as an occlusive dressing; and in such a case, wounds can be observed with far more difficulty. Because the binding of a complexing agent with polyvinyl alcohol is via physical crosslinking, steam sterilization cannot be applied. At a temperature where the hydrogel B is not solubilized, the gel generates many extracted products with low safety, disadvantageously. Thus, the gel is not suitable as a wound dressing. Hydrogel C may be transparent, depending on the conditions for producing the gel. However, the hydrogel C has poor workability because of weak physical strength. Additionally, a type of the hydrogel C, with a lower crosslinking degree, cannot be sterilized with hot steam. The hydrogel C generates many extracted products at a temperature where the hydrogel C is not solubilized, involving lower safety, disadvantageously. When the crosslinking degree is elevated, the hydrogel C is cleaved of the main chain with radiation and the water content and flexibility is decreased, disadvantageously. Thus, the hydrogel C is not suitable as a wound dressing. The hydrogel D, being transparent, has good mechanical strength which is preferable for medical use, but no examination has been made of the hydrogel D as a wound dressing.

It is an object of the present invention to provide a wound dressing having hot water resistance which can tolerate steam sterilization (at 121° C. for 20 minutes) and having an occlusive potency capable of retaining exudate and having excellent transparency, flexibility, water absorptivity, and safety.

SUMMARY OF THE INVENTION

In accordance with the present invention, the aforementioned object can be attained by providing a wound dressing composed of a hydrogel with the principal component being a vinyl alcohol polymer of a viscosity average polymerization degree of 300 or more, wherein the vinyl alcohol polymer contains 5 to 50 mol % of one or more vinyl ester units represented by the following formula (I):

wherein $R^1$ represents a hydrogen atom or a hydrocarbon group; $R^2$ and $R^3$ independently represent a hydrocarbon group; and $R^2$ and $R^3$, or $R^1$, $R^2$ and $R^3$, together with the carbon atom to which they are bound, may form a ring, and the vinyl alcohol polymer has a block character ($\eta$) of 0.6 or less, the block character being represented by the following mathematical formula (II):

$$\eta = [OH, VES]/2[OH][VES] \qquad (II)$$

wherein [OH, VES] represents the molar ratio of the methylene carbon between the methine carbon bound with a hydroxyl group and the methine carbon bound with an acyloxy group, to the total methylene carbons of the vinyl alcohol polymer; [OH] represents the molar ratio of the vinyl alcohol unit; and [VES] represents the molar ratio of the vinyl ester unit represented by the general formula (I).

The wound dressing of the present invention has hot water resistance capable of tolerating steam sterilization (at 121° C. for 20 minutes), an occlusive potency capable of retaining exudate, and additionally, excellent transparency, flexibility, water absorptivity, and safety.

Because the wound dressing of the present invention has higher transparency, the dressing makes it possible to observe the state of a wound, namely the presence or absence of bacterial infection, the appearance of the growth of dermal and epidermal cells while the dressing is applied to the wounds. Therefore, it is not necessary to remove the dressing to observe the wound state. Additionally, because the dressing has greater flexibility, the wound dressing can reduce extraneous physical irritation, causing less pain in a patient, while the dressing is applied to the wound. Because the wound dressing of the present invention has excellent water absorptivity, the dressing exerts a function of retaining body fluid, thereby controlling water vaporization. In other words, the wound dressing exerts a prominent effect of promoting the healing as an occlusive dressing. Still furthermore, because the dressing has excellent hot water resistance, the dressing can be sterilized in hot steam, with less extracted products, leading to greater safety.

Additionally, because a reactive hydroxyl group is in the wound dressing of the present invention, the group can be chemically modified via covalent bonding in various ways; and by controlling the ratio of the vinyl ester unit and the block character of the vinyl alcohol polymer as the principal component of the hydrogel, the transparency, flexibility, water absorptivity and physical strength of the dressing can be controlled. Thus, the wound dressing of the present invention can be given functions, for example a drug releasing function.

DETAILED DESCRIPTION OF THE PREFERRED EMBODIMENTS

In the general formula (I), the hydrocarbon group independently represented by $R^1$, $R^2$ and $R^3$ is preferably a hydrocarbon group with 1 to 18 carbon atoms (C1 to C18), for example, including an alkyl group such as methyl group, ethyl group, propyl group, n-butyl group, t-butyl group, octyl group, lauryl group or stearyl group; an aryl group such as phenyl group, naphthyl group or anthryl group; a cycloalkyl group such as cyclohexyl group, bicyclo[3.1.0] hexyl group or bicyclo[2.2.0]hexyl group. In the general formula (I), if $R^1$ and $R^2$, or $R^1$, $R^2$ and $R^3$, together with the carbon atom to which they are bound, form a ring, the ring may be saturated or unsaturated. Rings include a benzene ring, cyclohexane ring, norbornane ring, adamantane ring, noradamantane ring and the like.

The vinyl ester from which the vinyl ester unit represented by the general formula (I) is derived, includes, for example, vinyl trialkylacetate such as vinyl pivalate, vinyl dimethylethylacetate, vinyl dimethylpropylacetate, vinyl diethylmethylacetate, vinyl triethylacetate, vinyl tripropylacetate or vinyl versatate; vinyl dialkylacetate such as vinyl dimethylacetate, vinyl diethylacetate or vinyl dipropylacetate; vinyl ester with a cyclic hydrocarbon group such as vinyl methylcyclohexylacetate, vinyl 1-norbornanecarboxylate or vinyl 3-noradamantanecarboxylate.

The vinyl alcohol polymer in accordance with the present invention is required to have a viscosity average polymerization degree of 300 or more, preferably 800 or more, and more preferably 1500 or more, with respect to gel strength and processability. With respect to processability, furthermore, the upper limit of the viscosity average polymerization degree is preferably 50,000 or less. If the viscosity average polymerization degree is below 300, the mechanical strength and hot water resistance of the resulting wound dressing may be insufficient.

Herein, the viscosity average polymerization degree is calculated by the following mathematical formula (III), based on the intrinsic viscosity of polyvinyl acetate ([$\eta$] (dl/g); measured in acetone at 30° C.) produced by completely saponifying vinyl alcohol polymer and thereafter preparing the resulting saponified product into acetate:

$$\text{viscosity average polymerization degree} = ([\eta] \times 1000/7.94)^{(1/0.62)} \qquad (III)$$

In accordance with the present invention, vinyl alcohol polymer contains 5 to 50 mol % of the vinyl ester unit represented by the aforementioned general formula (I). If the content of the vinyl ester unit is above 50 mol %, the water content, flexibility and transparency of the gel as the component of the wound dressing is deteriorated. If the content is below 5 mol %, the hydrogel as the component of the wound dressing cannot acquire sufficient strength. Even if the hydrogel can be generated, the hot water resistance and transparency thereof is so severely deteriorated that the hydrogel cannot be used in a practical sense. Furthermore, the content of the vinyl ester unit of the vinyl alcohol polymer, which is represented by the general formula (I), can be determined by NMR in deuterated dimethyl sulfoxide.

In accordance with the present invention, the block character ($\eta$) of the vinyl alcohol polymer, defined by the mathematical formula (II), should be 0.6 or less. Furthermore, [OH, VES] in the mathematical formula (II) can be determined by $^{13}$C-NMR of the vinyl alcohol polymer. The block character ($\eta$) is the characteristic value of the distribution in the chain of the vinyl alcohol unit and the vinyl ester unit represented by the general formula (I) contained in the vinyl alcohol polymer and is a numerical figure from 0 to 2. In the case of a block copolymer, the value is near 0. In the case of a random copolymer, the value is 1. And in the case of an alternating copolymer, the value is 2. The vinyl alcohol polymer in accordance with the present invention is preferably a multi-block copolymer in terms of the transparency, water content and strength of the resultant gel. Hence, the block character (η) is preferably below 0.5, more preferably below 0.4. From a vinyl alcohol polymer with the block character (η) above 0.6, a hydrogel capable of constituting a wound dressing with satisfactory transparency, higher water retentivity and hot water resistance cannot be produced.

The vinyl alcohol polymer in accordance with the present invention should have a syndiotacticity of 55% or more, preferably 58% or more and far more preferably 60% or more, with respect to the hot water resistance of a hydrogel produced from the vinyl alcohol polymer. Herein, the term "syndiotacticity" means the syndiotacticity in the diad tacticity determined from the triad tacticity determined on the proton signal of the hydroxyl group in the proton NMR of completely saponified vinyl alcohol polymer in deuterated dimethyl sulfoxide by the following mathematical formula (IV):

$$syndiotacticity = S + H/2 \qquad (IV)$$

wherein S and H respectively represent the syndiotacticity and heterotacticity of the triad tacticity determined from the proton NMR.

In accordance with the present invention, the vinyl alcohol polymer is produced from the saponification of a homopolymer composed of the vinyl ester unit represented by the general formula (I), a copolymer composed of two or more vinyl ester units represented by the general formula (I), or a copolymer composed of one or more vinyl ester units represented by the general formula (I) with a structural unit derived from vinyl trifluoroacetate, vinyl trichloroacetate, vinyl formate, t-butyl vinyl ether, trimethylsilyl vinyl ether and the like. The saponification is carried out by a routine method, for example, a process comprising adding a solution of potassium hydroxide in methanol to a methanol solution of the polymer in a nitrogen stream for heating under agitation, to produce the vinyl alcohol polymer of the present invention. Then, the saponification degree can be adjusted by appropriately presetting the reaction temperature and reaction time.

The hydrogel with the principal component being the vinyl alcohol polymer can be produced, for example, by the process described below. 1 to 50% by weight of the vinyl alcohol polymer is dissolved in a water-soluble organic solvent or a mixture solvent of water and a water-soluble organic solvent. The resulting solution is poured onto a glass plate or the solution is charged into a glass tube or the solution is spinned from a nozzle or sprayed in the form of liquid micro-droplets, depending on the objective gel form. Subsequently, the resulting product is immersed into water, a water soluble organic solvent or a mixture solvent of water and a water-soluble organic solvent, to prepare the product into a gel. The gel is then immersed in a solvent including water, producing a transparent hydrogel, which is in the form of a plate, a cylinder, fiber or particles. Such water-soluble organic solvent includes any of those which can dissolve the vinyl alcohol polymer and are miscible with water, with no specific limitation. For example, use is made of dimethyl sulfoxide, N-methylpyrrolidone, 1,1,1,3,3,3-hexafluoro-2-propanol, dimethylformamide, dimethylacetamide, glycerin, ethylene glycol, n-propanol, isopropanol, ethanol and the like. These may be used singly or in combination with two or more thereof. A small amount of an inorganic salt may be added to these solvent systems for use. Besides the process described above, the hydrogel as the raw material of the wound dressing may be produced by other known processes such as radiation crosslinking and chemical crosslinking with a bifunctional reagent.

For the purpose of adjusting the water content and providing adhesiveness and the like, another ingredient other than the vinyl alcohol polymer may be added to the hydrogel in accordance with the present invention, during and/or after the process of producing the hydrogel, following a process such as immersion. Another ingredient other than the vinyl alcohol polymer includes any of those which neither inhibit the gelation of the vinyl alcohol polymer nor deteriorate the strength and transparency of the hydrogel, with no specific limitation, for example, including polysaccharide such as alginic acid or chitosan; polyamino acid such as polylysine, polyaspartic acid or polyglutamic acid; protein such as collagen, albumin or gelatin; synthetic polymers such as polyacrylate, polymethacrylate, ethylene-vinyl alcohol copolymer, polyvinyl acetate or polyethylene glycol; a low molecular compound such as ethylene glycol, glycerin, succinic acid or oxalic acid; and the derivatives or salts thereof.

By processing the hydrogel thus produced by a known process to prepare the gel into the form of powder, film, fiber, woven-fabric, non-woven fabric and the like, the wound dressing of the present invention can be produced. The hydrogel in the form of a plate, a cylinder, fiber or particles may be used, as it is, as a wound dressing.

Also, the hydrogel may be prepared into a wound dressing, by adding a pharmaceutically acceptable additive such as a softener and a stabilizer for the gel, or by adding a pharmaceutical agent or a physiologically active substance having an activity effective for wound healing—such as a pharmacologically active metal ion such as $Ca^{2+}$; an anti-microbial agent such as an antibiotic and sterilizer; a blood circulation improving agent such as actosin and PGE1; a growth factor such as TGFβ, PDGF, and FGF; an enzyme inhibitor such as urinastatin and TIMP; an anti-inflammatory agent such as steroid and a non-steroidal anti-inflammatory agent—to the gel, or by immobilizing the pharmaceutical agent or the physiologically active agent described above through an appropriate spacer or a linker which is cleaved in response to stimulation.

Because the wound dressing in accordance with the present invention has a satisfactory mechanical strength, the dressing is applicable as it is to wounds in the form of the hydrogel. Also, the gel may be used in the form of being attached to a medical grade film, such as a silicon film or polyurethane film; otherwise, the gel may be used in a dry- or freeze-dried state. For the purpose of increasing the adhesion thereof to a wound or tissues surrounding the wound, an adhesive may be coated onto or may be mixed with the gel.

It has been confirmed that the wound dressing of the present invention generates less extracted products because of the excellent hot water resistance; and lower toxicity of the dressing has been confirmed in toxicity tests. Additionally, it has been confirmed that the dressing can be subjected to steam sterilization.

EXAMPLES

Having generally described this invention, a further understanding can be obtained by reference to certain specific examples which are provided herein for purposes of illustration only and are not intended to be limiting unless otherwise specified.

Example 1

A partially saponified product of polyvinyl pivalate (a molar ratio of the vinyl ester unit of 7%; a syndiotacticity of 61% and a viscosity average polymerization degree of 1560; η=0.28) (3.5 g) was dissolved in dimethyl sulfoxide (100 ml), and the resulting solution was poured onto a glass plate, which was then immersed in water for gelation, followed by thorough washing in water to remove dimethyl sulfoxide. Subsequently, the water contained in the resulting hydrogel was substituted with physiological saline to prepare a transparent wound dressing in a sheet form.

Example 2

A partially saponified product of polyvinyl pivalate (a molar ratio of the vinyl ester unit of 19%; a syndiotacticity of 61% and a viscosity average polymerization degree of 1650; η=0.27) (5 g) was dissolved in N-methylpyrrolidone (100 ml), and the resulting solution was poured onto a glass plate, which was then immersed in water for gelation. As in Example 1, the gel was processed to prepare a transparent wound dressing in the form of a sheet.

Example 3

A partially saponified product of polyvinyl pivalate (a molar ratio of the vinyl ester unit of 37%; a syndiotacticity of 61% and a viscosity average polymerization degree of 1650; η=0.25) (4 g) was dissolved in dimethyl sulfoxide (100 ml), and the resulting solution was spun from a thin nozzle into water to prepare a hydrogel fiber. The fiber was then thoroughly washed in water prior to drying, which was then prepared into non-woven fabric according to a routine method. The resulting fabric was then immersed in physiological saline to prepare a wound dressing in the form of non-woven fabric.

Example 4

A partially saponified product of polyvinyl pivalate (a molar ratio of the vinyl ester unit of 19%; a syndiotacticity of 61% and a viscosity average polymerization degree of 1650; η=0.27) (5 g) was dissolved together with polyacrylate (1 g; the molecular weight of 450,000; manufactured by Wako Junyaku Co., Ltd.) in dimethyl sulfoxide (100 ml), and the resulting solution was poured onto a glass plate, which was then immersed in water for gelation. The gel was processed as in Example 1, to prepare a transparent wound dressing in the form of sheet.

Example 5

A partially saponified product of polyvinyl pivalate (a molar ratio of the vinyl ester unit of 19%; a syndiotacticity of 61% and a viscosity average polymerization degree of 1650; η=0.27) (5 g) and polyvinylpyrrolidone (1 g; Type K-90; a molecular weight of 360,000; manufactured by Wako Jyunyaku Co., Ltd.) were dissolved in dimethyl sulfoxide (100 ml), and the resulting solution was sprayed from a thin nozzle into n-hexane cooled to −20° C., which was immediately filtered and recovered, and was immediately dispersed in water for sufficient washing in water. Then, the substitution with physiological saline generates a wound dressing in the form of powder.

Comparative Example 1

The same procedure was carried out as in Example 1, except that a saponified product of polyvinyl acetate (a molar ratio of the vinyl ester unit of 12%, a syndiotacticity of 53%, a viscosity average polymerization degree of 1700 and η=0.51) was used, instead of the partially saponified product of polyvinyl pivalate in Example 1. The resulting product had such an extremely low strength that the product could not maintain the sheet form.

Comparative Example 2

A saponified product of polyvinyl acetate (a molar ratio of the vinyl ester unit of 1.5%; a syndiotacticity of 53% and a viscosity average polymerization degree of 1700; η=0.52) (5 g) was dissolved in an aqueous solution containing 10% glycerin under heating. The resulting solution was poured onto a polystyrene plate with projections, followed by freezing and dehydration under reduced pressure at −20 ° C., to prepare a polyvinyl alcohol hydrogel in a sheet form. The resulting opaque gel was thoroughly washed in water, prior to the substitution of the water contained in the gel with physiological saline, to prepare a wound dressing in a sheet form.

Comparative Example 3

A 5% solution of the saponified product of polyvinyl pivalate (a molar ratio of the vinyl ester unit of 0.1%; a syndiotacticity of 61% and a viscosity average polymerization degree of 1650; η=0.01) in dimethyl sulfoxide was poured onto a glass plate, which was then immersed in water for gelation, followed by thorough washing in water to substitute the water contained in the gel with physiological saline to prepare a sheet-form wound dressing. The gel was transparent and flexible immediately after the production, but the gel gradually shrunk in volume and turned white and opaque during water washing and storage, also involving the marked decrease of the flexibility thereof.

Comparative Example 4

A saponified product of polyvinyl acetate (a molar ratio of the vinyl ester unit of 1.5%; a syndiotacticity of 53% and a viscosity average polymerization degree of 1700; η=0.52) (10 g) was mixed with dimethyl sulfoxide (50 ml) and water (50 ml), prior to heating under agitation at 90° C. for 2 hours for dissolution. After cooling the resulting solution to 60° C., an aqueous 25% solution of poly(methyl vinyl ether/maleic anhydride) (20 ml; manufactured by Aldrich, Co.; low molecular weight) was added to the solution, for further agitation for 30 minutes. The resulting solution was poured onto a polystyrene tray and left to stand for cooling until the temperature reached room temperature, and subsequently, the solution was left to stand at −20° C. for 14 hours to prepare semi-transparent gel. The gel was sufficiently washed in water, and then, the water contained in the gel was substituted with physiological saline to prepare a sheet-form wound dressing.

Test Example 1

The following individual tests were carried out using the wound dressings produced in Examples 1 to 5 and the wound dressings produced in Comparative Examples 2 to 4. The results are shown in Table 1.

Hot water resistance

Each of the wound dressings was cut into pieces, each of about 2-cm square, which were then subjected to steam sterilization in physiological saline (at 121° C. for 20 minutes) to examine the appearance and workability of the wound dressings prior to and after the steam sterilization.

Transparency

Each of the wound dressings was filled in a physiological saline-filled spectrophotometric cell with a 1-cm light-path so that no space is present in the cell. The transmittance was measured at 700 nm with a Beckman Type DU-65 Spectrophotometer. The transmittance was defined as 100% when only physiological saline was filled therein.

Extracted products

To each (1 g) of the wound dressings was added physiological saline (10 ml), which was then heated and left to stand at 37° C. for 24 hours. The total organic carbon content (TOC) in the supernatant was determined.

Workability

Each of the wound dressings was cut into pieces, each of about 2-cm square, and examination was made as to whether or not individual pieces could be handled with a pair of tweezers. In Table 1, herein, o is marked for a wound dressing which is not damaged even if the dressing is held with the dental tweezers, while × is marked for a wound dressing which is damaged when the dressing is held with the dental tweezers.

Water absorptivity

The water absorption of each of the wound dressings in physiological saline was determined and expressed as the ratio of the dressing weight in water absorption to the dry weight.

Flexibility

Each of the wound dressings was cut into pieces, each of about 2-cm square, and examination was made as to whether one end of each piece could be held up easily with dental tweezers or spatula until the end was bent in contact to the other end. In Table 1, herein, o is marked for the piece when it can be easily bent while × is marked for the piece when it cannot easily be bent.

Test Example 2

Partial thickness defective wounds, each size thereof being 2 cm×2 cm, were made on the dorsal part of a Wister rat (of body weight of about 350 g). The wound dressings from Examples 1 to 5 were subjected to steam sterilization (at 121° C. for 20 minutes) in physiological saline, and the sterilized dressings were attached to the wounds to assess the extent of healing of the wounds over about 2 weeks. All of the average time periods required for healing the individual wounds attached with the respective wound dressings from Examples 1 to 5, were about 7 days. The effect of promoting the healing was observed, compared with the average time period for healing the wounds without any attachment, which was 9 days. During the whole testing period, the wounds could be observed through all of the wound dressings.

Test Example 3

The full-thickness defective wounds, each size thereof being 2 cm×2 cm, were made on a porcine dorsal part. After steam sterilization (at 121° C. for 20 minutes) in physiological saline, the wound dressing in a sheet form from Examples 2 was attached to six of the wounds. Alternatively, the wound dressings in sheet forms from Comparative Examples 2 and 4 were respectively attached to two of the wounds, while a commercially available polyurethane film dressing (BIOCLUSIVE, manufactured by Johnson & Johnson) was attached as the control to two of the wounds. The duration of such attachment was 5 to 6 days.

Results

During the testing period, the wounds could be observed through the wound dressing in the sheet form of Example 2 and the wound dressing in the sheet form of Comparative Example 4, but the wound could not be observed through the sheet-form wound dressing of Comparative Example 2 because the dressing was opaque.

Individual samples of the tissues on day 5 or 6 were stained with hematoxylin-eosin, to assess the extent of granulation growth and the intensity of the reaction of the tissues to foreign bodies, using as a control the commercially available polyurethane film dressing (BIOCLUSIVE, Johnson & Johnson). The results are shown in Table 1.

As shown in the aforementioned Test Examples, the wound dressing in accordance with the present invention when attached to wounds, burns, pressure sores, and the like, can treat the wounds or promote the healing thereof. Furthermore, the state of the wounds can be observed through the wound dressing as it is attached thereto without removing, so that the dressing is useful for wound management.

Obviously, numerous modifications and variations of the present invention are possible in light of the above teachings. It is therefore to be understood that within the scope of the appended claims, the invention may be practiced otherwise than as specifically described herein.

TABLE 1

| | $R^1$ | $R^2$ | $R^3$ | VINYL ESTER UNIT | Pn | η | GELATION | HOT WATER RESISTANCE | TRANSPARENCY | EXTRACTED PRODUCTS | WORK-ABILITY | WATER ABSORPTIV-ITY | FLEXIBILITY | GRANULATION | REACTION TO FOREIGN BODIES |
|---|---|---|---|---|---|---|---|---|---|---|---|---|---|---|---|
| EXAMPLE 1 | $CH_3$ | $CH_3$ | $CH_3$ | 7% | 1560 | 0.28 | ○ | ○ (NO CHANGE) | 38% | 0 | ○ | 9.2 | ○ | — | — |
| EXAMPLE 2 | $CH_3$ | $CH_3$ | $CH_3$ | 19% | 1650 | 0.27 | ○ | ○ (NO CHANGE) | 80% | 0 | ○ | 9.5 | ○ | GOOD | WEEK |
| EXAMPLE 3 | $CH_3$ | $CH_3$ | $CH_3$ | 37% | 1650 | 0.25 | ○ | ○ (NO CHANGE) | — | 0 | — | 3.0 | — | — | — |
| EXAMPLE 4 | $CH_3$ | $CH_3$ | $CH_3$ | 19% | 1650 | 0.27 | ○ | ○ (NO CHANGE) | 78% | 0 | ○ | 10.7 | ○ | — | — |
| EXAMPLE 5 | $CH_3$ | $CH_3$ | $CH_3$ | 19% | 1650 | 0.27 | ○ | ○ (NO CHANGE) | — | — | — | 11.0 | — | — | — |
| COMPARATIVE EXAMPLE 1 | H | H | H | 12% | 1700 | 0.51 | X | — | — | — | — | — | — | — | — |
| COMPARATIVE EXAMPLE 2 | H | H | H | 1.5% | 1700 | 0.52 | ○ | X (DISSOLVED) | 0.5% | 389.1 | ○ | 15.6 | ○ | GOOD | STRONG |
| COMPARATIVE EXAMPLE 3 | $CH_3$ | $CH_3$ | $CH_3$ | 0.1% | 1650 | 0.01 | ○ | X (DISSOLVED) | 0.5% | 2.5 | X (fragile) | 8.7 | X (hard) | — | — |
| COMPARATIVE EXAMPLE 4 | H | H | H | 1.5% | 1700 | 0.52 | ○ | X (DISSOLVED) | 29% | 51.5 | ○ | 32.9 | ○ | POOR | STRONG |

GELATION: ○ GELATION POSSIBLE; X GELATION IMPOSSIBLE
HOT WATER RESISTANCE; IN PHYSIOLOGICAL SALINE AT 121° C. FOR 20 min.
TRANSPARAENCY; TRANSMITTANCE AT 700 nm.
EXTRACTED PRODUCTS; TOTAL ORGANIC CARBON CONTENT (TOC IN ppm) IN THE SUPERNATANT IN PHYSIOLOGICAL SALINE AT 37° C., 24 HOURS LATER
WATER ABSORPTION; GEL WEIGHT IN PHYSIOLOGICAL SALINE/DRY WEIGHT
GRANULATION; REPRESENTED AS "GOOD" WHEN GRANULATION DEGREE IS LARGER THAN THAT OF COMMERCIALLY AVAILABLE POLYURETHANE FILM DRESSINGS; REPRESENTED AS "POOR" WHEN THE DEGREE IS SMALLER.
—: NOT DONE

What is claimed as new and is desired to be secured by Letters Patent of the United States is:

1. A wound dressing composed of a hydrogel whose principal component is a vinyl alcohol polymer of a viscosity average polymerization degree of 300 or more and having a syndiotacticity of 55% or more, wherein the vinyl alcohol polymer contains 5 to 50 mol % of one or more vinyl ester units represented by the following formula (I):

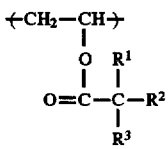    (I)

wherein $R^1$ represents a hydrogen atom or a hydrocarbon group; $R^2$ and $R^3$ independently represent a hydrocarbon group; and $R^2$ and $R^3$, or $R^1$, $R^2$ and $R^3$, together with the carbon atom to which they are bound, may form a ring, and wherein the vinyl alcohol polymer has a block character (η) of 0.28 or less, the block character being represented by the following mathematical formula (II):

$$\eta = \{OH, VES\}/2\{OH\}\{VES\} \quad (II)$$

wherein {OH, VES} represents the molar ratio of the methylene carbon between the methine carbon bound with a hydroxyl group and the methine carbon bound with an acyloxy group, to the total methylene carbons of the vinyl alcohol polymer; {OH} represents the molar ratio of the vinyl alcohol unit; and {VES} represents the molar ratio of the vinyl ester unit represented by the general formula (I).

2. The wound dressing according to claim 1, wherein each $R^1$, $R^2$ and $R^3$ is independently a hydrocarbon group with 1–18 carbon atoms.

3. The wound dressing according to claim 1, wherein the vinyl ester unit is derived from one or more vinyl esters selected from the group consisting of vinyl trialkylacetates, vinyl dialkylacetates and vinyl esters containing a cyclic hydrocarbon group.

4. The wound dressing according to claim 1, wherein the vinyl ester unit is derived from vinyl pivalate.

5. The wound dressing according to claim 1, wherein the viscosity average polymerization degree is 800 or more.

6. The wound dressing according to claim 1, wherein the viscosity average polymerization degree is 1500 or more.

7. The wound dressing according to claim 1, wherein the viscosity average polymerization degree is 50,000 or less.

8. The wound dressing according to claim 1, wherein the vinyl alcohol polymer has a syndiotacticity of 58% or more.

9. The wound dressing according to claim 1, wherein the vinyl alcohol polymer has a syndiotacticity of 60% or more.

10. The wound dressing according to claim 1, additionally containing another ingredient which neither inhibits the gelation of the vinyl alcohol polymer nor deteriorates the strength and transparency of the hydrogel.

11. The wound dressing according to claim 1, wherein the hydrogel is in the form of a powder, film, fiber, woven fabric or non-woven fabric.

12. The wound dressing according to claim 1, wherein the hydrogel is in the form of a plate, cylinder, fibers, or particles.

13. The wound dressing according to claim 1, additionally containing a pharmaceutically acceptable additive.

14. The wound dressing according to claim 1, additionally containing a physiologically active substance.

15. The wound dressing according to claim 1, additionally containing a film of another material attached to the hydrogel.

16. The wound dressing according to claim 15, wherein the film of another material is selected from the group consisting of silicon films and polyurethane films.

17. The wound dressing according to claim 1, wherein the hydrogel contains an adhesive coated onto or mixed therewith.

* * * * *